(12) United States Patent
Vapaavalta

(10) Patent No.: US 10,342,695 B2
(45) Date of Patent: Jul. 9, 2019

(54) DEVICE FOR COLD THERAPY

(71) Applicant: PKV HOUSING OY, Rovaniemi (FI)

(72) Inventor: Panu Vapaavalta, Rovaniemi (FI)

(73) Assignee: PKV HOUSING OY, Rovaniemi (FI)

( * ) Notice: Subject to any disclaimer, the term of this patent is extended or adjusted under 35 U.S.C. 154(b) by 0 days.

(21) Appl. No.: 14/373,104

(22) PCT Filed: Jan. 21, 2013

(86) PCT No.: PCT/FI2013/050063
§ 371 (c)(1),
(2) Date: Jul. 18, 2014

(87) PCT Pub. No.: WO2013/107942
PCT Pub. Date: Jul. 25, 2013

(65) Prior Publication Data
US 2015/0018903 A1 Jan. 15, 2015

(30) Foreign Application Priority Data
Jan. 19, 2012 (FI) ...................................... 20125061

(51) Int. Cl.
*A61F 7/00* (2006.01)
*A61H 33/00* (2006.01)
*A61H 35/00* (2006.01)

(52) U.S. Cl.
CPC .............. *A61F 7/00* (2013.01); *A61F 7/0085* (2013.01); *A61H 33/00* (2013.01);
(Continued)

(58) Field of Classification Search
CPC ............ A61F 7/0053; A61F 2007/0062; A61F 2007/0063
(Continued)

(56) References Cited

U.S. PATENT DOCUMENTS 4,773,471 A * 9/1988 Grant ................... A01K 1/0052
119/448
4,838,270 A * 6/1989 Donnerhack et al. .......... 607/83
(Continued)

FOREIGN PATENT DOCUMENTS

CN 2300406 12/1998
CN 1211906 3/1999
(Continued)

OTHER PUBLICATIONS

International Search Report dated Apr. 18, 2013, corresponding to PCT/FI2013/050063.
(Continued)

*Primary Examiner* — Joseph A Stoklosa
*Assistant Examiner* — Adam J Avigan
(74) *Attorney, Agent, or Firm* — Young & Thompson

(57) ABSTRACT

A device for cold therapy using cooling mist. Ice baths and cryogenic chamber are previously known solutions for cold therapy, but both suffer from several disadvantages, such as space requirements. The present device for cold therapy includes elements, such as a nozzle, for producing mist from liquid provided for the device, which mist stream is sprayed to a surface area of a treated object in order to cool the treated object, wherein the Sauter mean diameter of the mist is at most 150 μm.

17 Claims, 4 Drawing Sheets

(52) U.S. Cl.
CPC ..... *A61H 33/0095* (2013.01); *A61H 33/6036* (2013.01); *A61F 2007/0059* (2013.01); *A61F 2007/0062* (2013.01); *A61F 2007/0065* (2013.01); *A61F 2007/0068* (2013.01); *A61H 2035/004* (2013.01); *A61H 2201/0107* (2013.01); *A61H 2201/0161* (2013.01); *A61H 2201/0192* (2013.01); *A61H 2203/03* (2013.01); *A61H 2203/0406* (2013.01)

(58) Field of Classification Search
USPC .................................. 239/13, 373; 607/104
See application file for complete search history.

(56) References Cited

U.S. PATENT DOCUMENTS

| | | | | |
|---|---|---|---|---|
| 4,972,803 | A * | 11/1990 | Stump | 119/651 |
| 5,000,384 | A * | 3/1991 | Arnold | A47C 1/14 165/48.2 |
| 5,027,455 | A * | 7/1991 | Commisso et al. | 5/421 |
| 5,309,868 | A * | 5/1994 | Tomiyama | 119/203 |
| 5,337,960 | A * | 8/1994 | Allen | 239/280.5 |
| 5,535,951 | A * | 7/1996 | Utter | 239/322 |
| 5,598,719 | A * | 2/1997 | Jones et al. | 62/304 |
| 5,613,731 | A * | 3/1997 | Aspinall | A47C 1/14 239/289 |
| 5,620,140 | A * | 4/1997 | Utter | 239/153 |
| 6,081,944 | A * | 7/2000 | Edwards | B05B 15/06 239/209 |
| 6,161,362 | A * | 12/2000 | Forbis et al. | 52/745.06 |
| 6,195,814 | B1 * | 3/2001 | Yoshida | A47K 3/282 4/601 |
| 6,416,532 | B1 | 7/2002 | Fallik | |
| 6,454,190 | B1 * | 9/2002 | Cook | B01D 61/02 239/553 |
| 6,500,197 | B1 | 12/2002 | Buesselmann | |
| 6,581,855 | B1 * | 6/2003 | Cook | A62C 99/0072 239/548 |
| 6,592,049 | B1 * | 7/2003 | Wolput | B05B 1/202 239/211 |
| 6,886,759 | B1 * | 5/2005 | Okronick | A45B 3/00 239/16 |
| RE38,841 | E | 10/2005 | Yoshida et al. | |
| 7,077,465 | B1 * | 7/2006 | Calderon | A47C 1/14 297/180.15 |
| 7,252,329 | B1 * | 8/2007 | O'Meally | A47C 1/143 297/180.15 |
| 7,334,744 | B1 * | 2/2008 | Dawson | 239/373 |
| 8,881,998 | B1 * | 11/2014 | Sinkfield et al. | 239/172 |
| 2002/0193852 | A1 * | 12/2002 | Renfro | 607/104 |
| 2003/0097710 | A1 * | 5/2003 | Adrian | F24H 1/06 4/598 |
| 2004/0188544 | A1 * | 9/2004 | Pavlik | B63J 2/12 239/289 |
| 2005/0065582 | A1 * | 3/2005 | Blackburn | 607/104 |
| 2005/0077391 | A1 * | 4/2005 | Powell et al. | 239/373 |
| 2006/0173709 | A1 * | 8/2006 | Traynor | A61K 8/042 705/2 |
| 2007/0119969 | A1 * | 5/2007 | Collins et al. | 239/102.1 |
| 2007/0154405 | A1 * | 7/2007 | Malek | A61F 7/10 424/46 |
| 2008/0029016 | A1 * | 2/2008 | Axton | B63B 17/02 114/343 |
| 2008/0047291 | A1 * | 2/2008 | Colwell | B05B 7/0869 62/314 |
| 2008/0048051 | A1 * | 2/2008 | Chang | 239/289 |
| 2008/0128145 | A1 * | 6/2008 | Butz et al. | 169/46 |
| 2009/0072042 | A1 * | 3/2009 | Metcalf | F24F 5/0035 239/8 |
| 2009/0078795 | A1 * | 3/2009 | Levitsky | 239/463 |
| 2009/0108087 | A1 * | 4/2009 | Goldmann | F24F 6/12 239/1 |
| 2009/0192443 | A1 * | 7/2009 | Collins, Jr. | 604/24 |
| 2009/0212133 | A1 * | 8/2009 | Collins, Jr. | 239/338 |
| 2009/0293526 | A1 * | 12/2009 | Ichinomiya | F24F 3/1411 62/271 |
| 2010/0121418 | A1 * | 5/2010 | Lee et al. | 607/89 |
| 2010/0211140 | A1 | 8/2010 | Barbut et al. | |
| 2010/0237159 | A1 * | 9/2010 | Prater et al. | 239/1 |
| 2012/0241535 | A1 * | 9/2012 | Carriere et al. | 239/8 |

FOREIGN PATENT DOCUMENTS

| | | |
|---|---|---|
| CN | 1879904 | 12/2006 |
| FR | 2583280 | 12/1986 |
| FR | 2811222 | 1/2002 |
| JP | 2000225162 | 8/2000 |
| JP | 2005204712 | 8/2005 |
| JP | 2006-177578 A | 7/2006 |
| JP | 2006-346448 A | 12/2006 |
| JP | 2006346360 | 12/2006 |
| JP | 2010-096415 A | 4/2010 |

OTHER PUBLICATIONS

Finnish Search Report dated Oct. 15, 2012, corresponding to the Foreign Priority Application No. 20125061.
CN Office Action; dated Jul. 3, 2015; Application No. 201380006067X.
European search report, dated Sep. 25, 2015; Application No. 13738741.
Japanese Office Action issued in Application No. 2014-552668, dated Oct. 25, 2016 with English Translation.
Chinese Office Action for Application No. 2017111476316, dated Sep. 29, 2018, with English translation provided.

* cited by examiner

DEVICE FOR COLD THERAPY

TECHNICAL FIELD

Generally, the invention relates to a device for cold therapy. More specifically, the invention relates to a device for cold therapy using cooling mist.

BACKGROUND TECHNOLOGY

Cold therapy, such as ice bathing and cryogenic chamber therapy, is commonly used, especially in sports, wherein the cold therapy is a training regimen usually following a period of intense exercise. The cold therapy is claimed to prevent injuries and to help the body to recover faster from an intense period of activity. The cold therapy is known to influence blood vessels as tightening them and withdrawing blood to the body's core. After the cold therapy, the circulation of blood is suggested to be stimulated and oxygen and nutrient supply to e.g. inflamed and injured areas is claimed to be improved.

However, ice bathing and cryogenic chamber therapy has to be performed in closely monitored circumstances. Staying too long in an ice bath or in a cryogenic chamber may cause hypothermia or frostbites, or sudden exposure to extreme cold could harm patients with heart problems or asthma and, in a worst case, may even lead to sudden death. In addition, many people experience the ice bath as an unpleasant or even a painful event. By exposing the body to ice water can be an overwhelming accomplishment for some, even knowing the benefits of the treatment.

Moreover, even a small basin of ice bath is a heavy construction and needs a lot of water. Normally the volume of a basin is 200 L or more. If the ice bath is a permanent arrangement, the maintenance of the bath requires regular water changing and using of chemicals for keeping the water clean, which can be expensive and requires trained maintenance personnel. Used chemicals may also cause health or allergy problems or they can irritate bather's eyes and/or airways. In addition, the ice bath needs a cooling system to keep the required temperature, which consumes lot of energy and, thus, increases maintenance expenses.

Typically, the cold in a cryogenic chamber is produced with nitrogen in a form of vapor, which can be a more comfortable experience to a user than ice bathing. However, a cryogenic chamber needs a lot of room for the chamber itself and its equipment, as well as for the surveillance for users in the chamber. Like ice baths, using and maintaining the cryogenic equipment require training and personnel.

SUMMARY OF THE INVENTION

The purpose of the present invention is to avoid or, at least, reduce disadvantages of the prior art solutions described above.

The object of the invention is achieved with a solution, wherein the cold is directed to desired skin areas as a form of a cooling mist.

According to one embodiment, the device for cold therapy in accordance with the present invention comprises means, such as a nozzle, for producing mist from liquid provided for the device, which mist stream is sprayed to a surface area of a treated object in order to cool said treated object, wherein Sauter mean diameter of the mist is at most 150 μm.

According to another embodiment, the temperature of said liquid is below the normal human body temperature.

Yet, according to another embodiment, air stream is provided in connection with mist stream for improving the cooling effect in said surface area.

According to one embodiment, the device comprises at least one arm comprising at least one nozzle, which nozzle is connected to the liquid supply and configured to spray mist in a desired direction.

In one embodiment, the number of the nozzles in the arm is configurable. Yet, in another embodiment, the direction of the mist stream from a nozzle is adjustable. These embodiments enable using of the same device to various objects and in a different manner.

In another embodiment, the device comprises at least two arms, which arms are disposed relative to each other so that mist streams from the nozzles in the arms are arranged to collide. The collision of the mist streams provides a combined mist stream, which directs downwards.

Yet, in another embodiment, the distance between the arms in the device is adjustable. The adjustable distance between arms in the device may enable the using of the device to various purposes and/or in different circumstances. When the distance between the arms is adjustable, the same device can be used for treating a human, a dog and a horse, for example. Furthermore, the same device can be modified for treating a part of a body, such as a thigh, bag or whole body.

Yet, in another embodiment, the mist stream is adjustable by adjusting the pressure of liquid. In another embodiment, the droplet size of mist is adjustable by adjusting the settings of a nozzle.

In one embodiment, the used liquid is water. This feature is advantageous, because water is known to be absolutely safe for human and is usually available, which makes the using of the device easy. In many cases, the device just needs to be connected to a local water distribution system in a bathroom, for example.

Some preferable embodiments of the invention are described in the dependent claims.

Significant advantages can be achieved with the present invention when compared to the prior known solutions. The present invention is lightweight, easy to assemble and to use. Comparing to an ice bath, it does not need any water changing or may not require other maintenance procedures. Unlike a cryogenic chamber and an ice bath, the device for cold therapy according to the present invention may be implemented without heavy, solid structures and it may be configured to be collapsible, so it can be carried with and used wherever a water supply is available. In addition, it can also comprise its own water reservoir for providing liquid for the device. Furthermore, the device may diminish water consumption, because the cooling mist can be produced by using only a fraction of the water amount used for ice bathing, for example.

Because the present invention is hygienic and may be implemented without chemicals, the cold therapy according to the present invention may not cause any problems with health or allergies. This feature may also spare money and time, because chemicals can be expensive and using them requires time and training.

The adjustment and modification possibilities of the present invention may enable the invention to be applied for several objects and skin areas, such as a human body, animals, e.g. greyhounds and other dogs, race horses, etc., to a whole body usually the head excluded, single muscle or muscle group, such as thigh muscles, back muscles, arm muscles, etc. just to name a few.

To list some advantages of the cold therapy according to the present invention, the cold therapy may facilitate a healing process in an injured muscle or joint, and overall enhance the recovery process. In addition, the cold therapy may alleviate a pain and reduce inflammation and swelling in a body. The device according to the present invention may be used for pain treatment, which pain can be caused by an illness or an accident, for example.

Using of the device is easy and a person as well as an animal user may experience that cooling mist is more pleasant than a traditional ice bath. Moreover, cooling mist may not be painful for users and harmful for their health and cooling mist may not cause hypothermia or any frostbite to the user.

The cold therapy performed by using the present invention may also have another objective, such as a treatment for rheumatism, especially atrophic arthritis, fibromyalgia, osteoarthritis and depression to name a few.

Furthermore, the benefits of the cold therapy according to the present invention may comprise mental calming of the treated object, altogether, and hormonal effects, such as secretion of corticotropin, beta-endorphins, cortisol, endogenous opioids, norepinephrine, and other agonists of alpha adrenergic receptors. These hormonal effects are known to have positive benefits in many ways.

The other known benefits of the cold therapy may be, for example, the formation of brown fat cells in a treated body, which may be advantageous in many ways; brown fat cells may, for example, ease weight loss, improve the adjustment to cold weather and enhance stress tolerance. Recently researched hormone irisin may have a role, when a body converts white fat cells to brown fat cells, and, thus, replicating positive effects of exercise and diet. Additional advantage of the cold therapy according to the present invention may be the production of hormone irisin in the body.

In addition to the above mentioned solutions for using the device according to the present invention for healing and preventing injuries, treatment and alleviation for various illnesses and symptoms, hormonal therapy as well as producing brown fat cells, the device may be used as a first aid in burn injuries or for cooling down a body having too high body temperature, for example. The device is sufficiently small and lightweight to be included in first aid equipment, e.g. of ambulance, and it may be suitable for instant cooling of the burned skin area and tissues. In case of the burn injuries, the scalability of the device may be usable, when e.g. paramedics need to use it for various kinds of burns. The device may be easy to modify for present needs.

The expression "surface of the treated object" in this document refers herein to a skin or other outer covering of the body of a person or animal, which is treated with the device.

SHORT DESCRIPTION OF THE DRAWINGS

Next, the invention is described in more detail with reference to the appended drawings, in which FIG. 1 is a surface area to volume ratio as function of a radius of a droplet;

Same reference numerals are used in different figures to denote similar elements.

DETAILED DESCRIPTION OF THE EMBODIMENTS

According to an embodiment of the present invention a device for cold therapy comprises means, such as a nozzle, for producing mist from liquid provided for the device. Mist stream is sprayed to a surface area of a treated object in order to cool said treated object.

Figure 1:
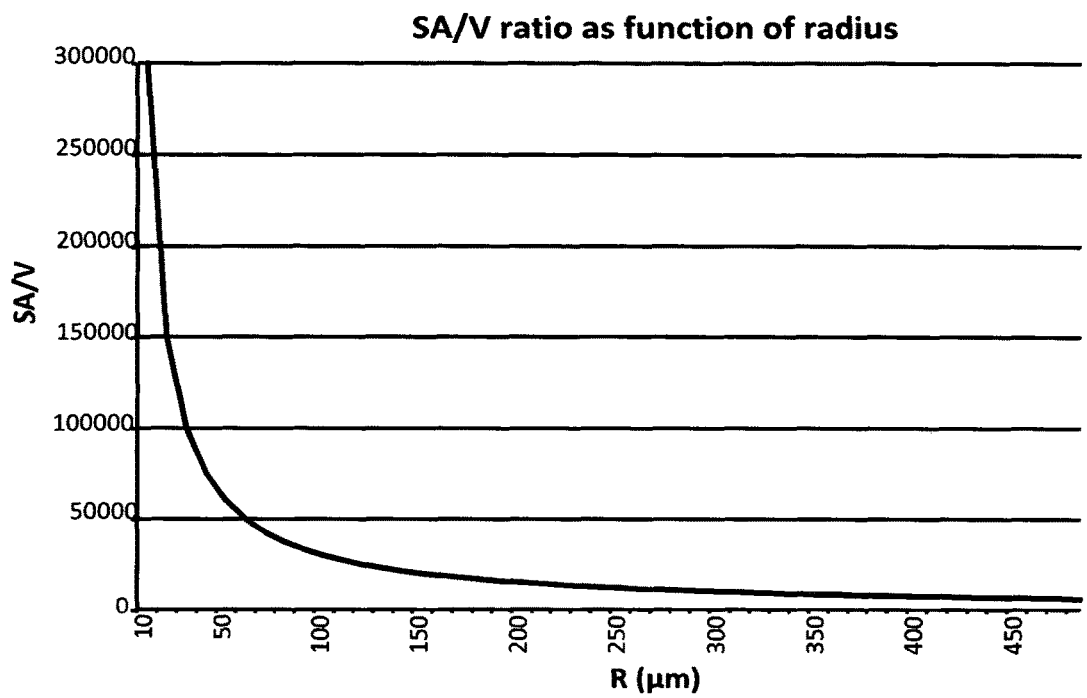

The cooling effect of mist in the present invention is based on the high enthalpy of vaporization of liquid, such as water. As can be seen in FIG. 1, fine mist, comprising a lot of small droplets, forms a large evaporation surface, which causes an efficient evaporation. Evaporation process requires energy (r=2256 kJ/kg), which is taken from heat of the surrounding air and the treated object. Due to the heat loss the treated object cools down.

The right droplet size of mist is essential in the present invention. Normally, Sauter mean diameter (SMD) is used to represent an average particle size in fluid dynamics. SMD is typically defined in terms of the surface diameter, $d_s$, and the volume diameter, $d_v$, as following $$SMD = \frac{d_v^3}{d_s^2}.$$

In this paper, SMD of mist is preferably about 15 μm-150 μm, more preferably about 30 μm-100 μm, and most preferably about 50 μm-80 μm. Mist having a greater SMD will not evaporate as well, because the area/volume ratio of a droplet decreases exponentially, when the radius of droplets increases, and the result will be more like normal shower with water drops without a sufficient evaporation effect. In that case, when using liquid having a sufficient low temperature, that shower can cool the treated object, but it can be very unpleasant experience and is based on cooling effect of cold water instead of evaporation of mist.

In addition, the number of the droplets applied to a skin area of the treated object affect to the cooling of the treated object. The number of the droplets highly depends on the size of the area and cannot be exactly defined. Advantageously, the treated area should be at least twice covered with droplets for achieving satisfactory cooling effect, but the person skilled in the art will understand that more mist droplets can also be used for cold therapy.

The temperature of the used liquid also affects to the cooling effect of mist. Depending on embodiment, the temperature of the used liquid can vary widely, for example between 0° C.-55° C., but preferably the temperature of the used liquid is below the normal human body temperature. In embodiments, wherein the treatment is directed to an animal, for example, the temperature of the used liquid is preferably selected to be under the normal body temperature of the treated animal in question.

In one embodiment, cold tap water is used as liquid in the present device. The temperature of cold tap water can vary, but preferably it is below 15° C., and, when altering water to mist, it may cool even more.

The device of the present invention can further comprise separate cooling means, such as carbon dioxide i.e. "dry ice", for cooling the used liquid, especially in summer. The other cooling means may also be used, but, preferably, cold tap water is adequate for cold therapy with the present device. When using a separate cooling means for cooling the used liquid, the liquid is preferably cooled before it is fed the hose system of the device. In another embodiment, the cooling and/or heating system is arranged in the hose system, e.g. between hose branches. This enables the use of the device for alternating treatment in such way that the water for the device is provided from the local water distribution system and heated/cooled to a desired temperature before alternating it to mist stream.

In another embodiment, the temperature of the used liquid is about 15° C. or more. In this embodiment, it is advantageous to control humidity of the space the device is used in. If relative humidity rises too high level, it substantially impairs the evaporation process of mist. Typically, humidity is controlled by arranging sufficient air ventilation in the space. As the person skilled in the art will understand, the air ventilation can also be arranged in connection with other embodiments.

In one embodiment, the used water supply is a local water distribution system and the water is directed to the hose system of the device with a normal pressure used in the water distribution system, typically e.g. about 3-4 bar. However, liquid having a higher pressure can also be used and it may be advantageous for producing mist having suitable droplet size. In that case, the pressure can be e.g. about 7 bar. If the local water distribution system does not provide a sufficient pressure, an additional pressure raising means can be used in connection with the device. The higher pressure is more efficient, because the required number of the droplets for the treated skin area is fulfilled faster.

The pressure of the liquid may also be adjustable in order to adjust the mist stream. In one embodiment, the device comprises means, such as pressurized air, for adjusting the pressure of the liquid used in the device.

In another embodiment, liquid, some other than water, is used for producing mist. The used liquid can be e.g., but not limited to, oil, milk, ethanol, lotion or water with nurturing ingredients, such as essential oils, perfumes, etc.

In another embodiment, the device is arranged to operate by using a separate water reservoir, such as a water canister, for example. In this case, the pressure in the hose system is arranged in some other manner, such as using separate pressurizing means, e.g. pressurized water canister or compressed air system. Normally, the separate water reservoir is sized for the use e.g. 40-50 L/h, and, the using time typically being e.g. 15-30 min, e.g. 25 L water canister can be adequate for one treatment, for example.

In an embodiment, air stream is provided in connection with mist stream. This feature can be implemented in various ways, but in one embodiment, both mist stream and air stream is provided in the same nozzle. In one embodiment, one or more used nozzles in the device are cone nozzles spraying mist stream in an angle, e.g. about 80 degrees, in a form of cone and spraying air stream in the middle of the nozzle.

The person skilled in the art will understand that air stream can also be provided some other way, such as dedicating one or more nozzles to air stream and others to mist stream, for example. The evaporation effect can further be improved by arranging a drainage system to the floor of the space, where the device is used. If waste water is removed, it does not evaporate to air and raise the humidity level.

An applying time of mist stream can vary depending on the size of the treated area and the meaning of the usage, but typically the device is used a couple of minutes, such as about 2 to 5 minutes, but the device can be used a longer time, especially if a larger surface area is about to be treated. The temperature of the surface of the treated object is intended to decrease several Celsius degrees, such as about 15° C.-26° C. For example, when a human is treated, the surface temperature of the treated area can be about 11° C. after the treatment.

Next, components and function of an exemplary device for cold therapy according to the present invention is discussed with reference to FIGS. 2-4.

An exemplary configuration of the device 100 for cold therapy comprises at least one arm 102, which arm 102 comprises at least one nozzle 104, which nozzle can be aimable. The nozzle 104 is connected to a liquid supply (not shown) and configured to spray mist in a desired direction.

Figure 2:
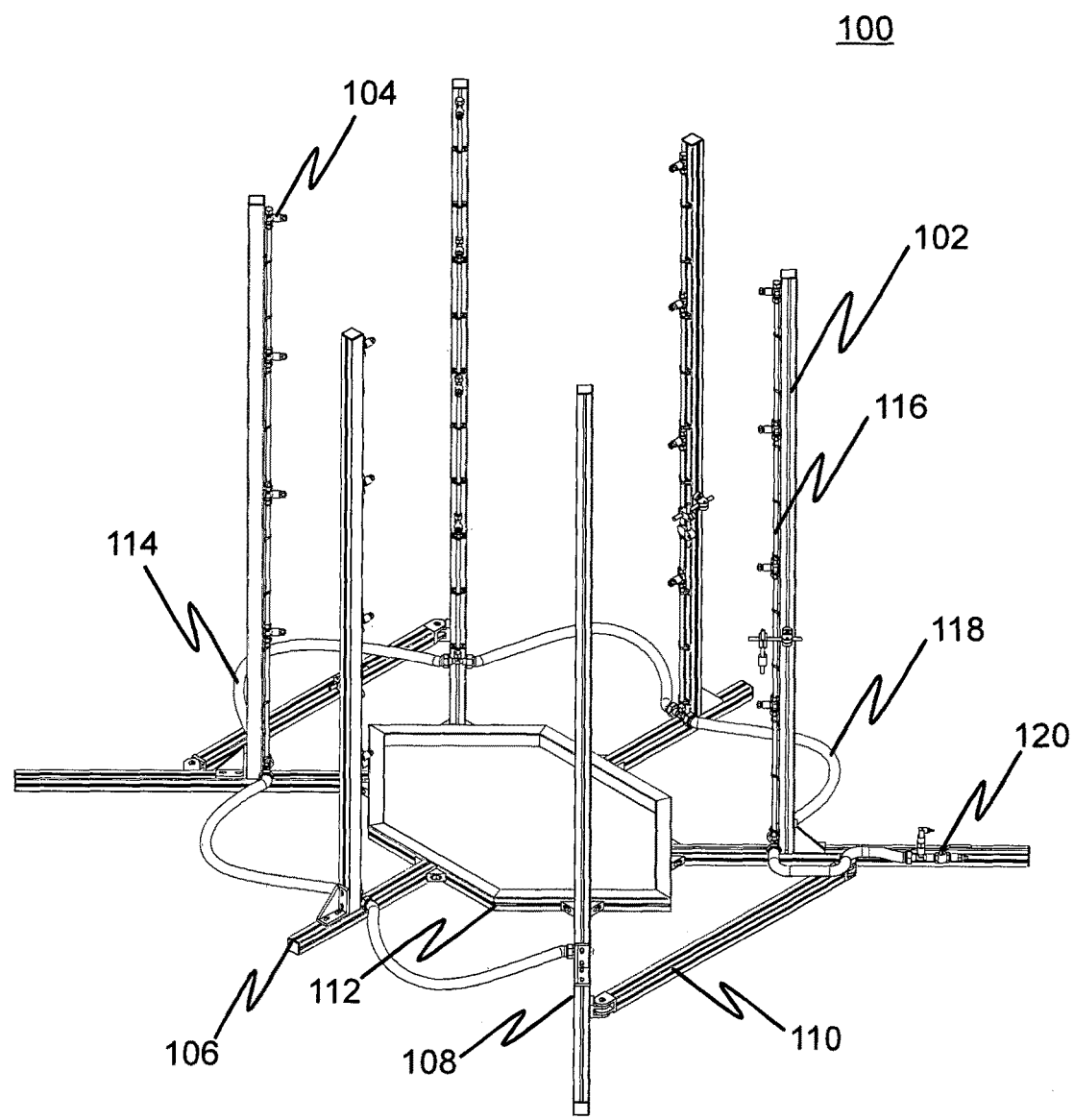
FIG. 2 depicts a perspective view of an exemplary device according to an embodiment of the present invention.
Figure 3:
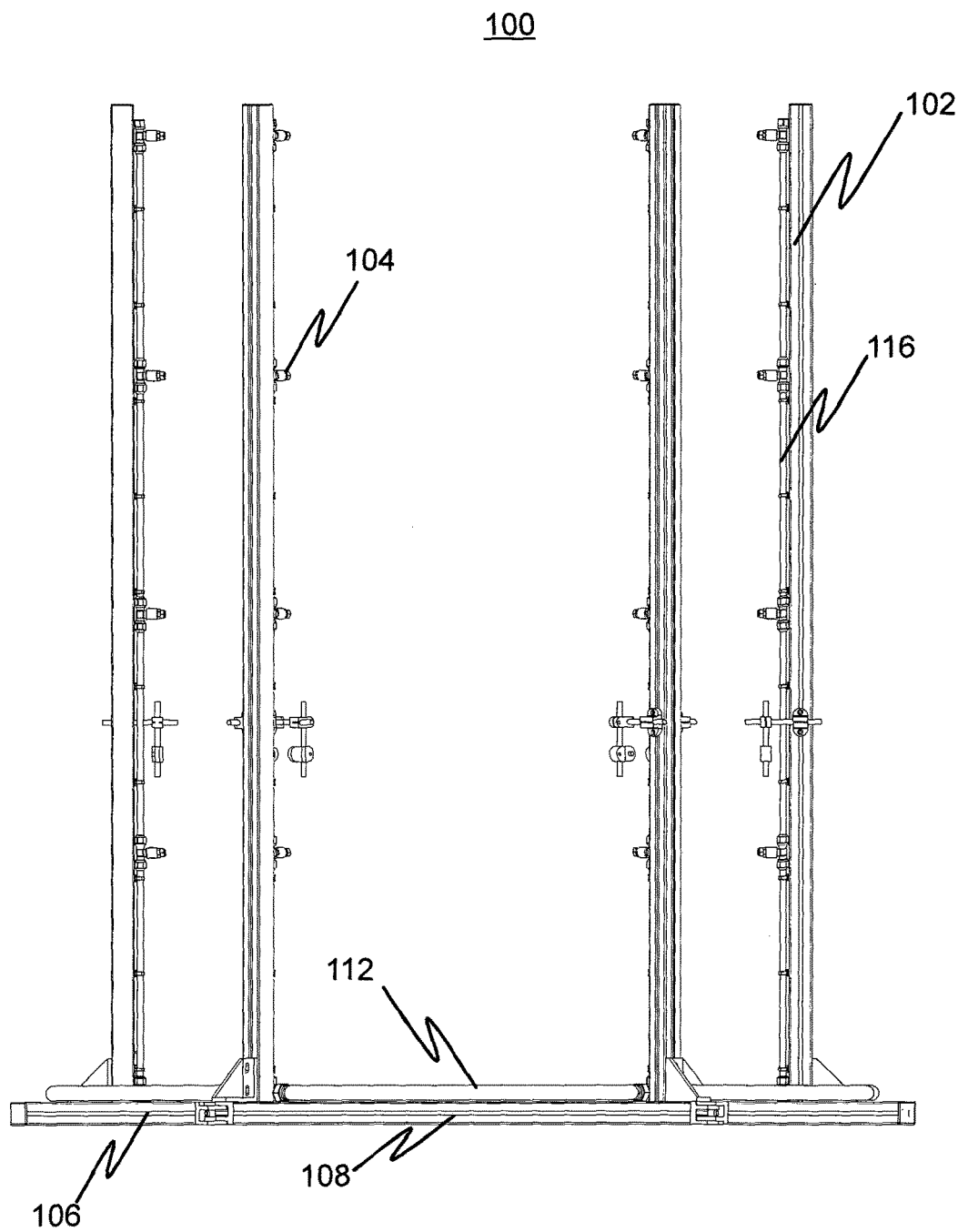
FIG. 3 depicts a side view of an exemplary device according to an embodiment of the present invention.
Figure 4:
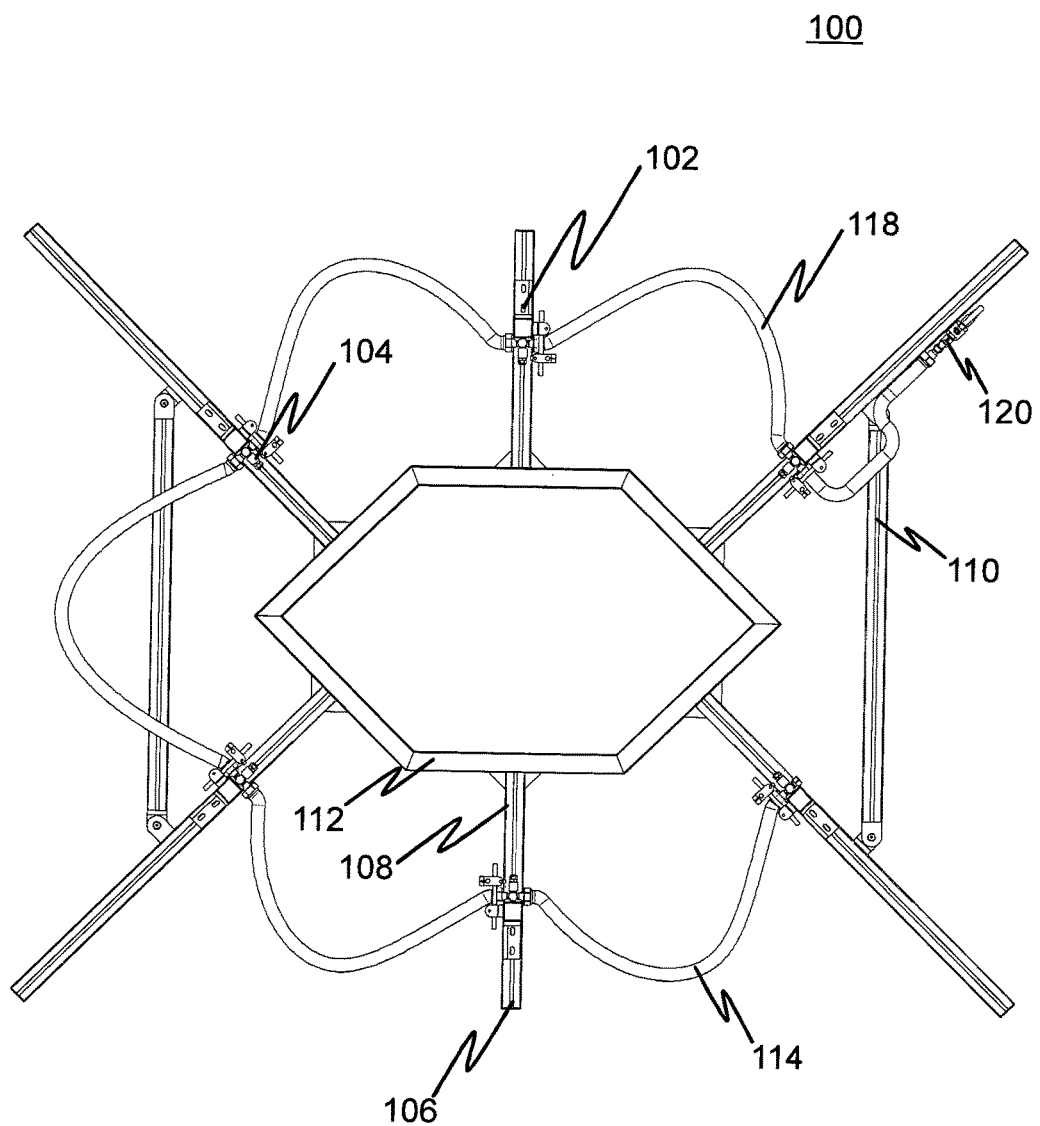
FIG. 4 depicts a top view of an exemplary device according to an embodiment of the present invention.

In an exemplary configuration of the device according to the present invention presented in FIGS. 2-4, the device 100 comprises six arms 102 arranged in a circle or in an oval form. The person skilled in the art will understand that the arms of the device can be arranged in some other appropriate form than above mentioned shapes. Depending on embodiment, the arms can be in a semicircular form or in a line, for example. In one additional embodiment, the arms are arranged to be detachable from the base structure, so that the arm can be used as a hand held device.

In a preferred embodiment, the number of arms is e.g. 4-6, but, depending on embodiment, the number of arms may be more or less. The device can be configured, so that the number and the position of arms can be changed, when the usage of the device changes.

Preferably, the arms are made from a durable, but lightweight material, such as aluminum, stainless steel or some other suitable material. The arms advantageously comprise means for attaching nozzles to the arm, such as clamps or some other suitable fasteners. Nozzles may also be fastened to an arm some other way, such as by using fast coupling means.

In some other embodiment, the nozzles comprise means for shutting and opening them, which enables the configuration of the number of used nozzles to be changed without detaching or attaching nozzles in the arm.

In FIGS. 2-4, each arm comprises four nozzles 104 aimed to spray mist stream to the centre of the circle. It should be obvious to the person skilled in the art that the number or the position of the nozzles in an arm or in the device can be changed freely depending on the use of the device. As well, in one embodiment, the arms have a telescopic structure, which enables the arms to be lengthened and/or shortened, when more or less nozzles are needed or when the position of a nozzle/nozzles is/are changed.

The nozzles 104 can be any appropriate nozzle for producing mist. In a preferable embodiment, the nozzles are adjustable so that the droplet size produced by the nozzle is changeable.

Typically, the nozzles 104 in the arms are arranged in different levels, so that object to be treated is sprayed with mist streams in several levels. If the object to be treated is a human, the nozzles are typically adjusted so that mist covers the person's whole body leaving the head out. It is characteristic for the mist stream that the stream turns downwards when hitting a solid object, such as a treated body, or when collided with another mist stream, in which case the streams combine and the combined stream turns downwards.

In one embodiment, the levels of the nozzles 104 in the arms 102 is selected so that the nozzles 104 in different arms 102 are disposed substantially in the same level. In that case, two or more mist streams can be arranged to collide so as to form a combined downwardly directed stream. By using this feature a larger mist stream can be provided in order to treat a part of the body, a lying person and/or an animal, for example.

In the exemplary device presented in FIGS. 2-4, the arms are further connected to foot parts 106 forming a base frame 108, which is intended to keep the device 100 in a substantially upright position. The position of the arms can be some other than upright, e.g. an angle with the ground level. The base frame is advantageously arranged to lie on the floor, which provides the needed support to the arms used in the upright position. In addition, two side braces 110 are connected between foot parts 106 in order to improve the support provided by the base frame 108.

In addition, the foot parts 106 of the base frame 108 may further be connected to a centre part 112, which can define a treatment area for treated person to stand. The centre part can further prevent or at least reduce water leakage from the treatment area. In some embodiment, a sensor or sensors are provided to centre part for observing the water temperature, for example. It should be obvious to the person skilled in the art that the device according to the present invention can be implemented without the centre part and the centre part can be an auxiliary or additional component in the device.

Like the arms, the base frame and the components thereof are made from a durable, but lightweight material, such as aluminum, stainless steel or some other suitable material. The foot parts 106 can comprise e.g. a groove for adjusting the position and distance between the arms. In addition, the foot parts can comprises means for fastening the arms to the base frame. However, the person skilled in the art understands that the device can also be implemented without a base frame or any other support part. In some embodiments, the device is configured so as to be held in a hand, for example.

The nozzles are further connected to a water supply. Preferably, water is provided to the nozzles via a hose system 114, which, typically, comprises connecting means 120 suitable for to be connected a local water distributing system. The water can be provided to each arm with a larger hose 118, which is used to connect the hose branch 116 or hoses between the arms 102. In some embodiments, the hose system 114 is integrated to the arms 102 and/or the base frame 108. In that case, a nozzle may be possible to add or remove from an arm without any arrangement in the hose system. In another embodiment, each nozzle is connected to a hose or a hose branch 116 and hoses or the hose branch 116 can be fastened to the arm or just the nozzles are fastened and the hoses/hose branch are left to hang freely.

In some auxiliary or additional embodiments, the device also comprises heating means. Usually, in that case, the device is used for altering treatment by alternately using cold mist and hot mist. In that case, one water type or both water types can be provided for the device from a separate reservoir/reservoirs. Separate reservoir can be advantageous, because hot water can be heated to a desired temperature and provided from the separate reservoir to the device. In some embodiments suitable for altering treatment, some nozzles can be dedicated to hot water and the others to cold water.

In some embodiments, the device further comprises one or more temperature/pressure sensors for monitoring and/or ensuring the temperature and/or the pressure of the used liquid.

Figure 5:
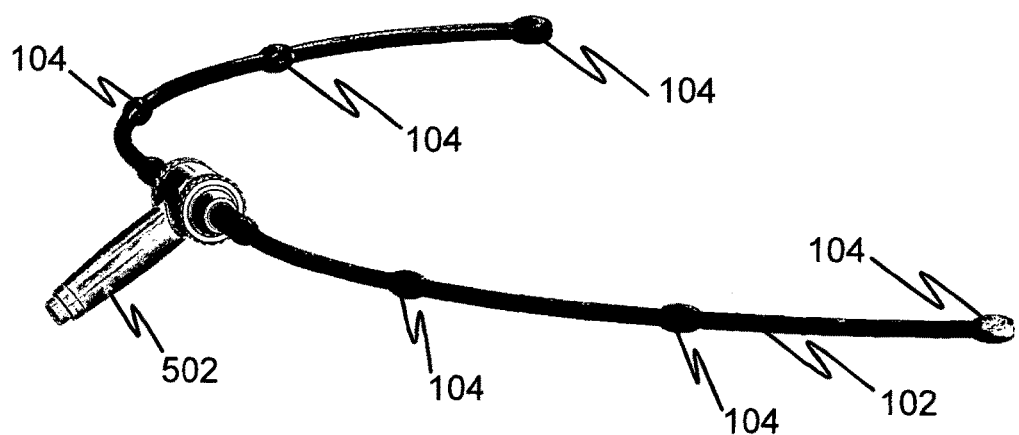
FIG. 5 depicts another exemplary device according to an embodiment of the present invention.

FIG. 5 depicts another exemplary device according to an embodiment of the present invention. In the present figure, it can be seen how the device according to the present invention can be attached to a regular shower arm instead of or in addition to a shower head. In the present embodiment, the device comprises a member 502, which can be attached to the shower arm. In this configuration, six nozzles 104 are connected to the arm 102 to provide mist stream to both sides of a user.

Although, the description concerns to using of the present for cold therapy, it is possible to use the device for washing instead of a traditional shower. Using the device for washing requires typically several nozzles, which may be arranged in several levels, e.g. 3-4 levels, or in one level for producing sufficient amount of mist, so that the washing procedure is pleasant experience and the water amount is adequate for washing and rinsing. The used water temperature can be selected to be higher than the used water temperature for cold therapy. The easiest way to provide warmer water for the device is to connect the hose system to a warm water supply. As described above, the water heating system can also be used for heating the water for washing.

The configuration of the device, i.e. the number and the location of the nozzles, as well as droplet size of the mist, the number of the arms, the base frame construction are selected so that the use of the device is kept in mind. The aim is to produce a thick mist stream(s) suitable for the present purpose, e.g. treating a part of the body, the whole body or various objects in various dimensions. However, it is not desired to produce mist streams that are not needed in that time, because that is a waste of water. Therefore the device of the present invention is usually enabled to be adjusted in different ways within the scope of the invention, as described above.

The scope of the invention is determined by the attached claims together with the equivalents thereof. The skilled persons will again appreciate the fact that the explicitly disclosed embodiments were constructed for illustrative purposes only, and the scope will cover further embodiments, embodiment combinations and equivalents that better suit each particular use case of the invention.

The invention claimed is:

1. A device for providing cold therapy to a skin area, the device comprising:
   a liquid supply that provides liquid at a temperature below 15° C.;
   means for producing a mist stream from said liquid provided from the liquid supply at a temperature below 15° C.,
   said means for producing a mist stream being configured to spray the mist stream onto a surface area of an area of a skin of a treated object in order to cool the skin at the skin area of said treated object by a cooling effect of said mist stream, said mist stream comprising mist particles,
   wherein Sauter mean diameter of the mist particles is in a range from 30 μm through 100 μm;
   means for producing an air stream, wherein the mist stream is provided in connection with the air stream for improving the cooling effect in said skin area; and
   at least two arms, each arm comprising at least one nozzle, the at least one nozzle being connected to the liquid supply and configured to spray the mist stream in a desired direction to the skin area to be cooled by the mist, the at least two arms being disposed relative to each other so that the mist streams from the nozzles in each arm are arranged to collide with the mist streams from the nozzles of the other arms, wherein at least one direction of said at least two arms and a direction of the mist stream from the at least one nozzle, is adjustable.

2. The device for providing cold therapy according to claim 1, wherein the liquid supply comprises a local water distribution system.

3. The device for providing cold therapy according to claim 1, wherein each arm comprises a plurality of nozzles, and plural of the nozzles in the plurality of nozzles in each arm is configurable.

4. The device for providing cold therapy according to claim 1, wherein the liquid is cooled by way of an apparatus for cooling the liquid prior to the liquid passing through the nozzle.

5. The device for providing cold therapy according to claim 4, wherein the apparatus for cooling the liquid comprises dry ice.

6. The device for providing cold therapy according to claim 4, wherein the apparatus for cooling the liquid comprises a cooling system.

7. The device for providing cold therapy according to claim 1, wherein the mist stream is adjustable by adjusting a supply pressure of the liquid.

8. The device for providing cold therapy according to claim 1, wherein the liquid is water.

9. The device for providing cold therapy according to claim 1, wherein the liquid comprises milk.

10. The device for providing cold therapy according to claim 1, wherein the liquid comprises a lotion.

11. The device for providing cold therapy according to claim 1, wherein the liquid comprises a perfume component.

12. The device for providing cold therapy according to claim 1, wherein, the liquid supply comprises a water canister in fluid communication with each arm and sized to provide 40-50 liters/hour for a period of at least 15 minutes and no more than 30 minutes, and the liquid is comprised of water and one of the group consisting of milk, a lotion, and a perfume.

13. A device for providing cold therapy to a skin area, the device comprising:

a liquid supply that provides liquid at a temperature below 15° C.;

a central part that defines a treatment area on which an object may stand;

at least four arms extending vertically above a level of the central part and arranged around the central part surrounding the central part, each of the at least four arms comprising plural nozzles, each nozzle being connected to the liquid supply to receive the liquid provided from the liquid supply at a temperature below 15° C., each nozzle producing a respective mist stream from said liquid provided from the liquid supply at the temperature below 15° C., each said mist stream comprising mist particles having a Sauter mean diameter in a range from 30 μm through 100 μm, each nozzle being direction adjustable to spray the respective mist stream in a desired direction toward and onto a skin area of the object standing on the central part to thereby cool the skin area with the mist stream by a cooling effect of said mist stream;

and an air system operatively connected to the at least four arms to provide an air stream from each of the at least four arms in connection with the mist stream from each of the at least four arms for improving the cooling effect in the skin area, wherein at least a first nozzle of a first of the arms is arranged at a same level as a first nozzle of a second of the arms, the first nozzles of the first and second arms being positioned so that at least the mist stream from the first nozzle of the first arm collides with the mist stream from the first nozzle of the second arm and where the mist streams from the first arm collide with the mist streams from the second arm.

14. The device for providing cold therapy according to claim 13, wherein the liquid is comprised of water and one of the group consisting of milk, a lotion, and a perfume.

15. The device for providing cold therapy according to claim 13, wherein the liquid is comprised of milk.

16. The device for providing cold therapy according to claim 13, wherein the liquid is comprised of a lotion.

17. The device for providing cold therapy according to claim 13, wherein the liquid comprises a perfume.

* * * * *